(12) United States Patent
Mantell

(10) Patent No.: US 10,086,154 B2
(45) Date of Patent: Oct. 2, 2018

(54) HIGH-FLOW LUER LOCK CONNECTOR FOR A LUER LOCK CONNECTION

(71) Applicant: Robert R. Mantell, Arlington Heights, IL (US)

(72) Inventor: Robert R. Mantell, Arlington Heights, IL (US)

(73) Assignee: Northgate Technologies Inc., Elgin, IL (US)

( * ) Notice: Subject to any disclaimer, the term of this patent is extended or adjusted under 35 U.S.C. 154(b) by 1071 days.

(21) Appl. No.: 14/076,842

(22) Filed: Nov. 11, 2013

(65) Prior Publication Data

US 2014/0066840 A1 Mar. 6, 2014

Related U.S. Application Data

(63) Continuation of application No. 12/776,647, filed on May 10, 2010, now Pat. No. 8,613,738, and a continuation of application No. 11/418,838, filed on May 5, 2006, now Pat. No. 7,740,288.

(60) Provisional application No. 60/679,452, filed on May 9, 2005.

(51) Int. Cl.
*A61M 39/10* (2006.01)
*A61M 13/00* (2006.01)

(52) U.S. Cl.
CPC .......... *A61M 13/003* (2013.01); *A61M 39/10* (2013.01); *A61M 2039/1033* (2013.01); *A61M 2202/025* (2013.01); *A61M 2202/0225* (2013.01); *A61M 2202/0283* (2013.01)

(58) Field of Classification Search
CPC .................................................. A61M 39/10

USPC .............. 285/332, 332.1, 332.2, 332.3, 355; 604/533, 538, 539

See application file for complete search history.

(56) References Cited

U.S. PATENT DOCUMENTS

| 4,133,312 A | 1/1979 | Burd |
| 4,294,250 A * | 10/1981 | Dennehey ............. A61M 39/10 604/403 |
| 4,369,781 A | 1/1983 | Gilson et al. |
| 4,824,145 A | 4/1989 | Carlsson |
| 5,092,854 A | 3/1992 | Black |
| 5,147,336 A | 9/1992 | Wendell et al. |
| 5,176,415 A | 1/1993 | Choksi |
| 5,312,377 A * | 5/1994 | Dalton .................. A61M 39/10 285/331 |
| 5,364,377 A | 11/1994 | O'Neil |
| 5,509,911 A | 4/1996 | Cottone et al. |
| 5,549,583 A | 8/1996 | Sanford et al. |

(Continued)

FOREIGN PATENT DOCUMENTS

WO WO 9116938 11/1991

*Primary Examiner* — James M Hewitt, II
(74) *Attorney, Agent, or Firm* — Brinks Gilson & Lione

(57) ABSTRACT

A high-flow luer lock connector is disclosed. A high-flow luer lock connector comprises a connector body defining an interior region, a lumen, and an extended passageway. The interior region is bounded by a cylindrical side wall and a base wall. The lumen is defined at the base wall of the interior region and extends no more than 0.274 of an inch into the interior region. The extended passageway comprises a first and second end and passes through the connector body and the lumen. The extended passageway is in communication with the interior region to allow insufflation gas to flow through the interior region and extended passageway.

10 Claims, 6 Drawing Sheets

(56) References Cited

U.S. PATENT DOCUMENTS

| | | |
|---|---|---|
| 5,599,328 A | 2/1997 | Stevens |
| 5,616,203 A | 4/1997 | Stevens |
| 5,620,427 A | 4/1997 | Werschmidt et al. |
| 5,651,776 A | 7/1997 | Appling et al. |
| 5,702,374 A | 12/1997 | Johnson |
| 5,782,505 A | 7/1998 | Brooks et al. |
| 5,947,954 A | 9/1999 | Bonaldo |
| 5,967,569 A | 10/1999 | Vaillancourt et al. |
| 6,193,692 B1 | 2/2001 | Harris et al. |
| 6,843,513 B2 | 1/2005 | Guala |
| 7,241,285 B1 | 7/2007 | Dikeman |
| 2002/0115984 A1 | 8/2002 | Guala |

\* cited by examiner

HIGH-FLOW LUER LOCK CONNECTOR FOR A LUER LOCK CONNECTION

RELATED APPLICATIONS

The present application is a continuation of U.S. patent application Ser. No. 12/776,647 (now U.S. Pat. No. 8,613,738), filed May 10, 2010, which is a continuation of U.S. patent application Ser. No. 11/418,838 (now U.S. Pat. No. 7,740,288), filed May 5, 2006, which claims the benefit of the filing date under 35 U.S.C. § 119(e) of Provisional U.S. Patent Application Ser. No. 60/679,452, filed May 9, 2005, the entirety of each of which are hereby incorporated herein by reference.

TECHNICAL FIELD

The present invention relates to medical devices. More specifically, this invention relates to luer lock connectors for use in insufflation systems.

BACKGROUND

Surgeons have used laparoscopic surgery to perform a variety of procedures. By manipulating laparoscopes and video telescopes, surgeons gain a visualization of the abdominal cavity while minimizing tissue and muscle injury that normally accompanies conventional invasive procedures.

To create a sufficient area for the introduction of a laparoscope and other instruments, the abdominal wall is first raised from the organs enclosed in the abdominal cavity. Separation is conventionally attained by pressurizing the abdominal cavity with an insufflation gas. The presence of artificial gas in the peritoneal cavity to achieve exposure during laparoscopy is referred to as pneumoperitoneum.

When maintaining pneumoperitoneum, it is desirable on occasion to infuse the insufflation gas into the cavity at a rate typically above 20 liters per minute. However, achieving this rate is often difficult. One of the primary limitations in providing higher insufflation gas flow rates are the constraints placed upon the insufflation equipment by common industry practice, efficacy requirements, and guidance documents issued by the United States Food and Drug Administration concerning issues such as push pressures, pressure duration, overshoot, and pressure relief. Insufflators normally are limited to a push pressure of about 45 to 55 millimeters of mercury. This limitation makes it difficult to infuse insufflation gas at the desired higher flow rates. Furthermore, the equipment associated with laparoscopic procedures such as luers, often restrict the infusion rate of insufflation gas.

Standardized luer lock connectors form secure, leak-free connections for the transfer of fluids or gasses between two devices or objects such as veress needles, trocars, syringes, or gas/fluid delivery systems. Although there are many luer lock connector sizes available, luer lock connections typically operate in the same way, and conform to International Organization of Standard ("ISO") standards 594-1 or 594-2.

A luer lock connection typically includes two luer lock connectors, known as a male luer lock connector and a female luer lock connector. As shown in FIG. 1, a first luer lock connector 102 (also known as a male luer lock connector) dimensioned to conform to ISO standards 594-1 and 594-2 comprises a connector body 104 defining an interior region 106 bounded by a cylindrical side wall 108 and a base wall 110, and an extended central lumen 112 extending at least 7.5 mm (0.2953 of an inch) into the interior region 106. The connector body 104 further defines a channel 114 passing through the extended central lumen 112 and the connector body 102 at the base wall 110. The channel 114 allows a substance to flow into the channel 114 at the extended central lumen 112 and pass through the connector body 102 via the channel 114 in one embodiment, or pass through the connector body 102 via the channel 114 and out of the central lumen 112 in another embodiment.

As seen in FIG. 2, to establish a luer lock connection 101, a second luer lock connector 118 (also known as a female luer lock connector) is inserted into the interior region 106 of the first luer lock connector 102, causing a plurality of threads 116 on the cylindrical side wall 108 of the first luer lock connector 102 to engage lugs or a plurality of threads 120 on an exterior of the second luer lock connector 118. The engagement between the plurality of threads 116, 120 of the first and second luer lock connectors 102, 188, draws the second luer lock connector 120 into the interior region 106 of the first luer lock connector 102 and draws the extended central lumen 112 into an open end 122 of the second luer lock connector 120 until the tapers of the first and second luer connectors 102, 120 are secured together.

Securing the first and second luer lock connectors 102, 120 together provides a basic leak-free connection for a substance such as insufflation gas to flow through the luer lock connector. However, the leak-free connection comes at the cost of a reduction in the flow speed of the substance flowing through the luer lock connector and a buildup of pressure before the luer lock connection due to the taper of the male and female components. Therefore, it would be desirable to have a luer lock connection that provides a basic leak-free connection with less reduction in flow speed or a buildup of pressure.

BRIEF SUMMARY

Accordingly, the present invention is directed to a high-flow luer lock connector for use within an insufflation system. In a first aspect, a high-flow luer lock connector comprises a connector body defining an interior region, a lumen, and an extended passageway. The interior region is bounded by a cylindrical side wall and a base wall. The lumen is defined at the base wall of the interior region and extends no more than 0.274 of an inch into the interior region. The extended passageway comprises a first and second end and passes through the connector body and the lumen. The extended passageway is in communication with the interior region to allow insufflation gas to flow through the interior region and extended passageway.

In a second aspect, a high-flow luer lock connector comprises a connector body defining an interior region and an extended passageway. The interior region is bounded by a cylindrical side wall and a base wall. The extended passageway comprises a first end and a second end and passes through the connector body at the base wall such that the first end of the extended passageway is flush with the base wall. The extended passageway way is in communication with the interior region to allow insufflation gas to flow through the interior region and extended passageway. Additionally, an o-ring is positioned in the interior region on the base wall surrounding at least the first end of the extended passageway.

In a third aspect, a luer lock connector comprises a connector body defining an interior region, a lumen rim, and an extended passageway. The interior region is bounded by a cylindrical side wall and a base wall. The lumen rim is defined at the base wall and extends no more than 0.125 of an inch into the interior region. The extended passageway comprises a first end and a second end and passes through the connector body and lumen rim such that the first end is flush with the lumen rim. The extended passageway is in communication with the interior region to allow insufflation gas to flow through the interior region and extended passageway.

In a fourth aspect, a luer lock connector comprises a connector body comprising elastomeric material defining an interior region and an extended passageway. The interior region is bounded by a conic side wall and a base wall. The extended passageway comprises a first end and a second end and passes through the connector body at the base wall such that the first end of the extended passageway is flush with the base wall. The extended passageway is in communication with the interior region to allow insufflation gas to flow through the interior region and extended passageway.

DETAILED DESCRIPTION OF THE DRAWINGS

Figure 1:
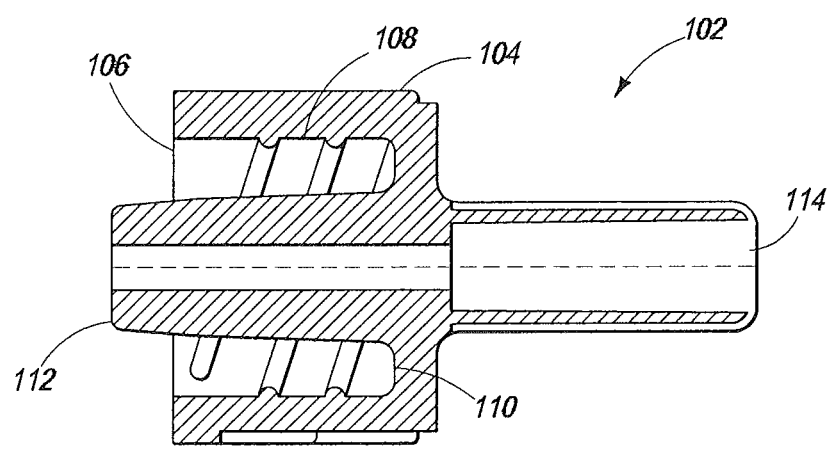
FIG. 1 is a side view of a cross-section of a prior art male luer lock connector.
Figure 2:
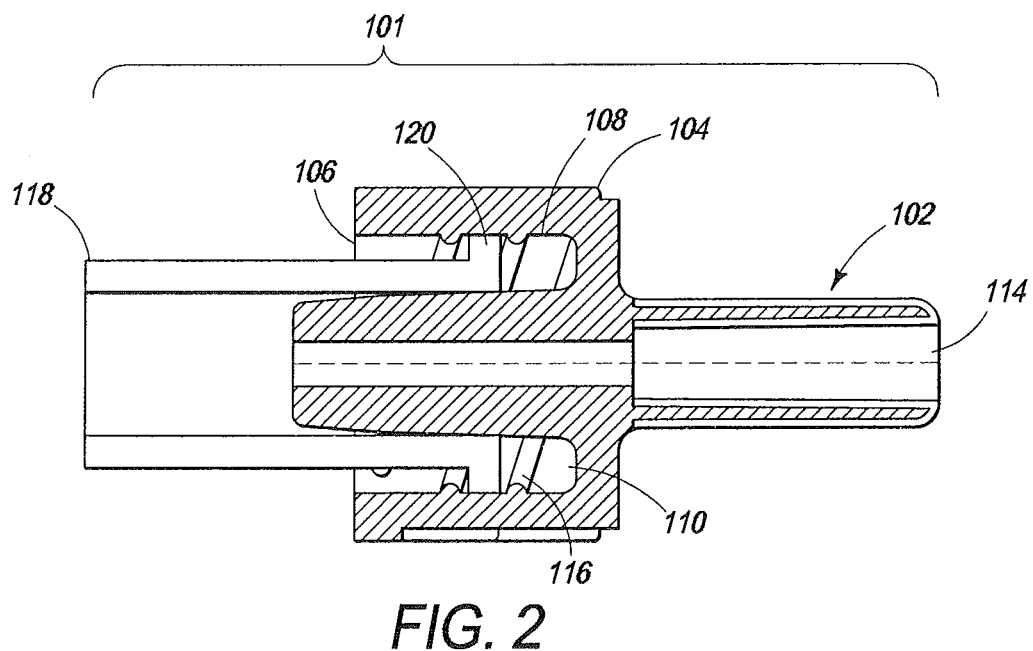
FIG. 2 is a side view of a cross-section of a luer lock connection.
Figure 3:
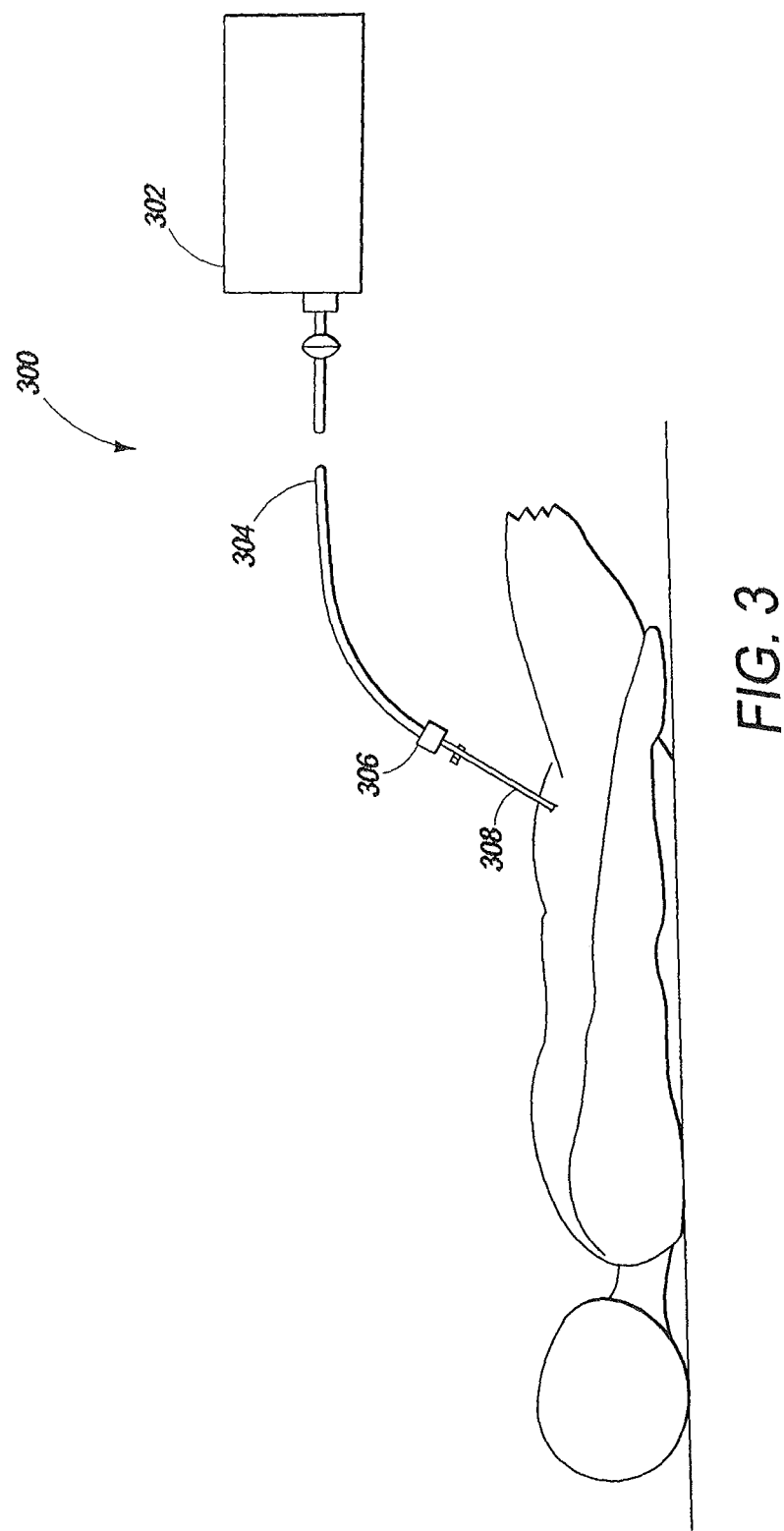
FIG. 3 is a diagram of a typical insufflation system.
Figure 4:
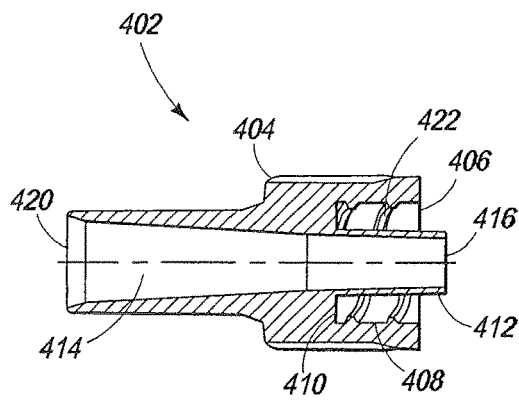
FIG. 4 is a side view of a cross-section of a first embodiment of a high-flow luer lock connector.
Figure 5:
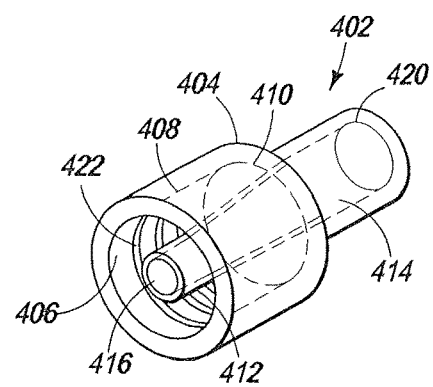
FIG. 5 is a perspective view of the high-flow luer lock connector of FIG. 4.
Figure 6:
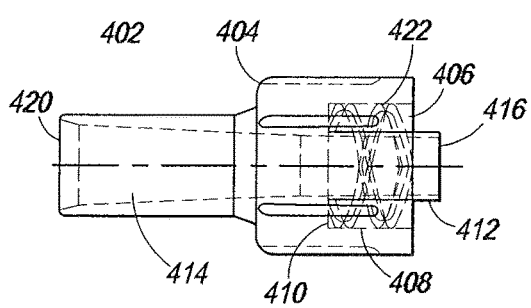
FIG. 6 is a side view of the high-flow luer lock connector of FIG. 4.
Figure 7:
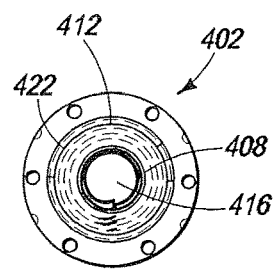
FIG. 7 is a front view of the high-flow luer lock connector of FIG. 4.
Figure 8:
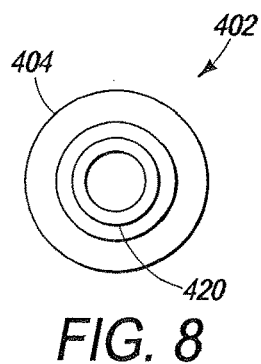
FIG. 8 is a rear view of the high-flow luer lock connector of FIG. 4.

FIG. 3 shows a typical insufflation system 300 comprising an insufflator 302, a tubing set 304, a luer connection 306, and a veress needle or trocar 308. Generally, insufflation gas is passed from the insufflator 302 to the veress needle or trocar 308 via the tubing set 304 and luer connection 306. Additionally, insufflation gas may be vented from the patient from the veress needle or trocar 308 to the insufflator 302 via the tubing set 304 and luer connection 306.

The insufflator 302 may be any type of insufflator such as the OMNIFLATOR Model 6620 available from Northgate Technologies, Inc. in Elgin, Ill. or a mixed-gas insufflator as disclosed in U.S. patent application Ser. No. 10/829,485, filed Apr. 22, 2004, the entirety of which is incorporated herein by reference. The insufflator 302 is typically in communication with a pressurized source of insufflation gas such as carbon dioxide, nitrous oxide, argon, or helium. During operation, the insufflator 302 typically reduces the pressure of the insufflation gas and delivers the insufflation gas to the tubing set 304, which serves as a delivery path for the insufflation gas.

The tubing set 304 may be any type of tubing set for use with an insufflation system such as a dual-capacity insufflation tube disclosed in U.S. patent Ser. No. 10/696,675, filed Oct. 28, 2003, the entirety of which is incorporated herein by reference. Additionally, the veress needle or trocar 308 may be any type of veress needle or trocar for use with an insufflation system such as an Ethicon Endo-Surgery's XCEL trocar or a laparoscopic insertion device disclosed in U.S. patent application Ser. No. 09/841,125, filed Dec. 5, 2002, the entirety of which is incorporated herein by reference.

Traditional luer lock connectors are comprised of male and female luer lock connectors such as a Qosina Model 71629 male luer. As described above, a traditional male luer lock connector in a luer lock connection 306 comprises an extended lumen that reduces the cross-sectional area through which a substance such as insufflation gas flows due to the tapering and wall thickness of the extended lumen. The reduction in cross-sectional area causes a decrease in flow rate through the luer lock connection and the buildup of pressure before the luer lock connector. In order to sustain flow rate and prevent the buildup of pressure, the high-flow luer lock connectors disclosed herein remove, or substantially reduce, the extended lumen in the design of a male luer lock connector. Additionally, the high-flow luer lock connectors disclosed herein decrease the wall thickness of the lumen to sustain a greater cross-section area for a substance to flow through. Typically, the high-flow luer lock connectors described herein can sustain a flow rate of greater than 26 liters per minute.

FIGS. 4-8 show a first embodiment of a high-flow luer lock connector 402. The high-flow luer lock connector 402 comprises a connector body 404 that defines an interior region 406 bounded by a cylindrical side wall 408 and a base wall 410. At the base wall 410, the connector body 404 further defines a lumen 412 that extends into the interior region 406.

Typically, the lumen 412 extends no more than 0.274 of an inch into the interior region 406 in contrast to standard male luers which comprise a lumen extending approximately 0.2953 of an inch into the interior region of the luer. Further, the lumen 412 typically has a wall thickness of 0.008 of an inch in contrast to standard male luers which comprise a lumen having a wall thickness of approximately 0.016 of an inch. However like standard male luers, the lumen 412 of the high-flow luer connector 402 tapers approximately 6 degrees to conform to ISO standards 594-1 and 594-2.

The connector body 404 additionally defines a rigid or semi-rigid extended passageway 414 comprising a first end 416 and a second end 420. The extended passageway 414 passes through the lumen 412 and the connector body 404 such that the first end 416 of the extended passageway 414 is positioned at the end of the lumen 412. Typically, the first end 416 has an inner diameter of approximately 0.131. Additionally, the second end 420 typically has an inner diameter of approximately 0.259 of an inch and may comprise a taper, chamfer, or any other type of shape to reduce resistance created by a substance flowing into or out of the second end 420.

Typically, the extended passageway 412 is operative to allow a substance to flow in either of two directions. In a first direction, a substance flows into the extended passageway 414 at the first end 416, flows through the lumen 412 and connector body 404 via the extended passageway 414, and flows out of the extended passageway 414 at the second end 420. In a second direction, a substance flows into the extended passageway 414 at the second end 420, flows through the connector body 404 and lumen 412 via the extended passageway 414, and flows out of the extended passageway 414 at the first end 416. These directions will generally correspond to introducing insufflation gas into an abdominal cavity of a patient or venting insufflation gas from the abdominal cavity of the patient.

The connector body 404 additionally defines a plurality of threads 422 on the cylindrical wall 408 operative to receive lugs or a plurality of threads defined on a corresponding female luer connector and place the corresponding female luer connector in position within the high-flow connector 402.

Figure 9:
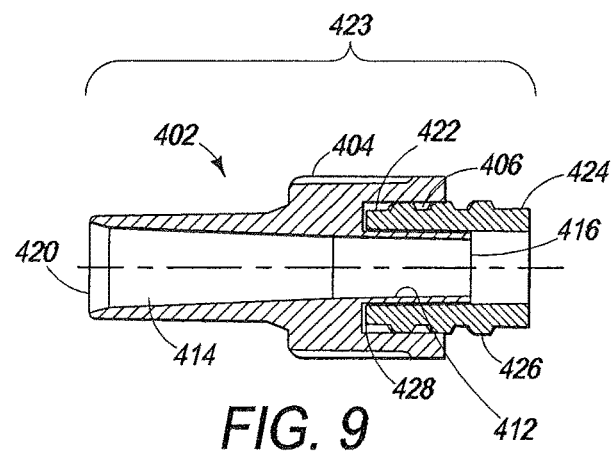
FIG. 9 is a side view of a cross-section of a luer lock connection utilizing the luer lock connector of FIG. 4.
Figure 10:
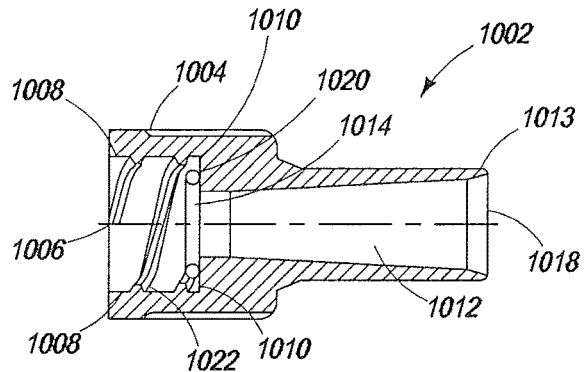
FIG. 10 is a side view of a cross-section of a second embodiment of a high-flow luer lock connector.
Figure 11:
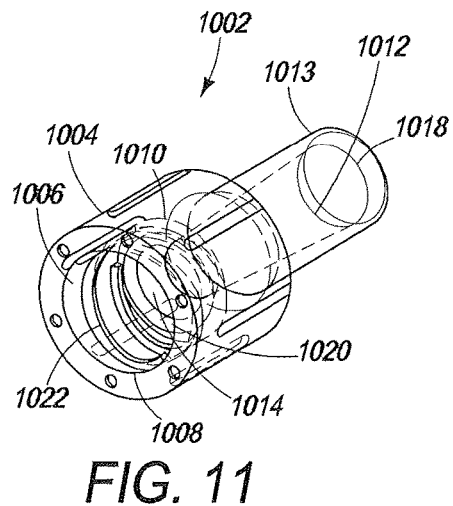
FIG. 11 is a perspective view of the high-flow luer lock connector of FIG. 10.
Figure 12:
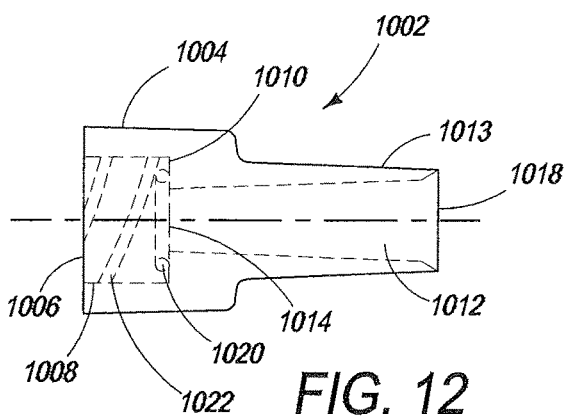
FIG. 12 is a side view of the high-flow luer lock connector of FIG. 10.
Figure 13:
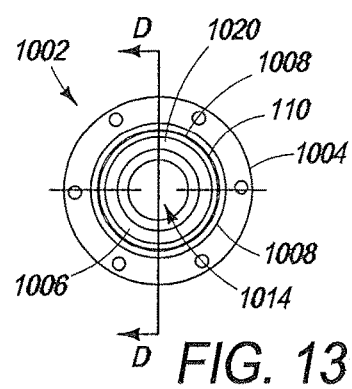
FIG. 13 is a front view of the high-flow luer lock connector of FIG. 10.
Figure 14:
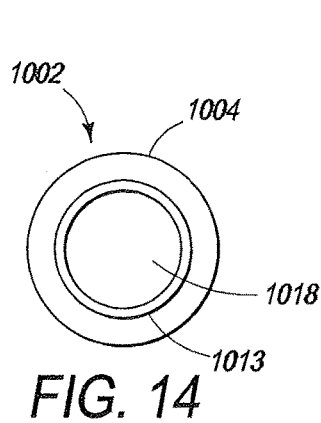
FIG. 14 is a rear view of the high-flow luer lock connector of FIG. 10.

As shown in FIG. 9, to establish a luer lock connection 423 a female luer lock connector 424 dimensioned according to ISO standards 594-1 or 594-2 is inserted into the interior region 406 of the high-flow luer lock connector 402 of FIGS. 4-8 causing the lugs or plurality of threads 426 on an exterior of the female luer lock connector 424 to engage the plurality of threads 422 of the high-flow luer lock connector 402.

Typically, the female luer lock connector 424 comprises a tapered open end 428 through which a substance may flow into or out of the female luer lock connector 424. The engagement of the plurality of threads 422, 426 draws the female luer lock connector 424 into the interior region 406 of the high-flow luer lock connector 402 and draws the lumen 412 into the open end 428 of the female luer lock connector 424 until the tapers of the lumen 412 and the open end 428 of the female luer lock connector 424 engage. When the tapers of the lumen 412 and the open end 428 of the female luer lock connector 424 engage, the lumen 412 seals against an interior of the female luer connector 424, thereby placing the open end 428 of the female luer lock connector 424 in communication with the extended passageway 414.

Due to the shortened lumen 412 as compared to standard male luers, the lumen 412 of the high-flow luer lock connector 402 may engage and seal against the interior of the female luer connector 424 more quickly than standard male luers. Thus, the lumen may sustain a wider cross-sectional area through which the substance flows through the luer lock connection 423, thereby preventing a substantial reduction in flow speed and a build up pressure.

FIGS. 10-14 show a second embodiment of a high-flow luer lock connector 1002. The high-flow luer lock connector 1002 comprises a connector body 1004 that defines an interior region 1006 bounded by a cylindrical side wall 1008 and a base wall 1010. The connector body 404 may be comprised of metal, rubber, or plastics such as Cyrolite plastic, manufactured by Cyro Industries.

The connector body 1004 further defines a rigid or semi-rigid extended passageway 1012 fixed relative to the connector body 1004 such that the portion of the connector body 1004 defining the extended passageway 1012 does not rotate independent of the remaining connector body 1004. An exterior of the connector body defining the extended passageway 1013 may be smooth, barbed, tapered, threaded, or have any other surface topography to assist the extended passageway 1012 in securing a conduit to it. The extended passageway 1012 comprises a first end 1014 and a second end 1018. The first end 1014 is flush with the base wall 1010 such that the extended passageway 1012 does not extend into the interior region 1006. Additionally, the second end 1018 may comprise a taper, chamfer, or any other type of shape to reduce resistance created by a substance flowing into or out of the second end 1018.

Typically, the extended passageway 1012 is operative to allow a substance to flow in either of two directions. In a first direction, a substance flows into the first end 1014 of the extended passageway 1012, passes through the connector body 1004 via the extended passageway 1012 and out of the extended passageway 1012 at the second end 1018. In a second direction, a substance flows into the second end 1018 of the extended passageway 1012, passes through the connector body 1004 via the extended passageway 1012 and out of the extended passageway 1012 at the first end 1014. These directions will generally correspond to introducing insufflation gas into an abdominal cavity of a patient or venting insufflation gas from the abdominal cavity of the patient.

An o-ring or compliant washer 1020 is positioned in the interior region 1006 at the base wall 1010 that surrounds at least the first end 1014 of the extended passageway 1012. Typically, the o-ring or washer 1020 will extend at least 0.0156 of an inch into the interior region 406, but no more than 0.09375 of an inch. The o-ring or washer 1020 may comprise rubber, silicone, PVC, or any other material operative to provide a seal to the surface of the mating female luer connector to prevent fluids or gasses from leaking around the o-ring 1020 or passing through the o-ring 1020 itself.

The connector body 1004 additionally defines a plurality of threads 1022 on the cylindrical wall 1010 operative to receive lugs or a plurality of threads defined on a corresponding female luer connector and place the corresponding female luer connector in position within the high-flow connector 1002.

Figure 15:
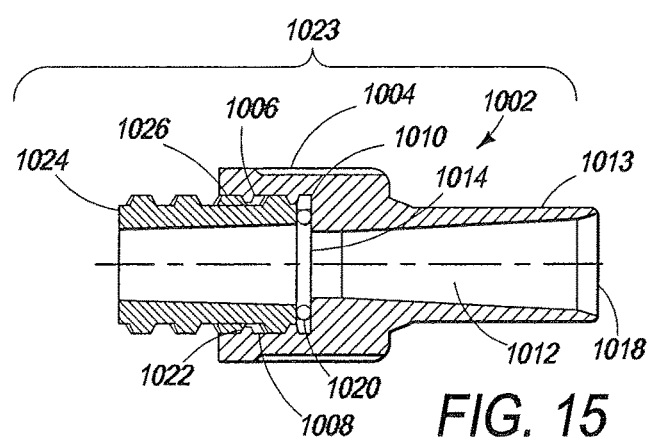
FIG. 15 is a side view of a cross-section of a luer lock connection utilizing the luer lock connector of FIG. 10.
Figure 16:
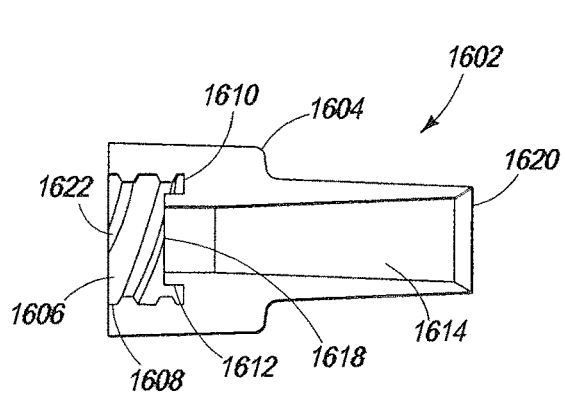
FIG. 16 is a side view of a cross-section of a third embodiment of a high-flow luer lock connector.
Figure 17:
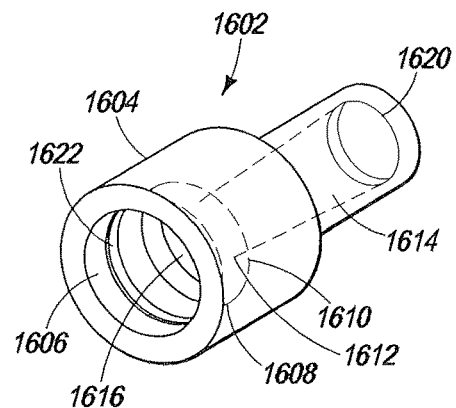
FIG. 17 is a perspective view of the high-flow luer lock connector of FIG. 16.
Figure 18:
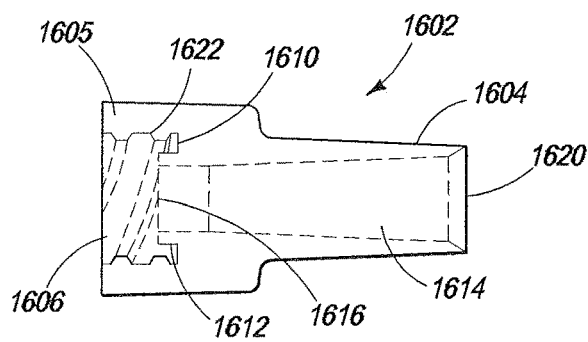
FIG. 18 is a side view of the high-flow luer lock connector of FIG. 16.
Figure 19:
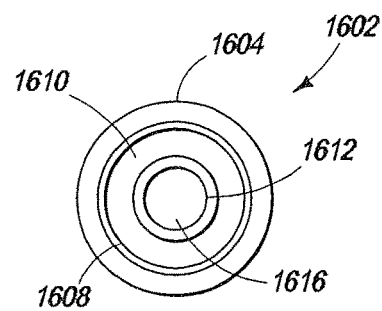
FIG. 19 is a front view of the high-flow luer lock connector of FIG. 16.
Figure 20:
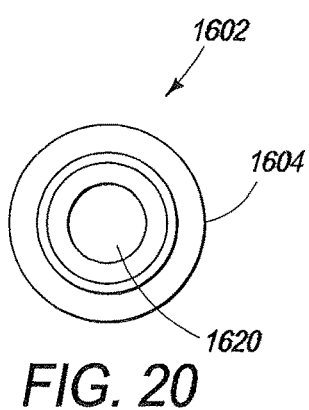
FIG. 20 is a rear view of the high-flow luer lock connector of FIG. 16.

As shown in FIG. 15, to establish a luer lock connection 1023 a female luer lock connector 1024 dimensioned according to ISO standards 594-1 or 594-2 is inserted into the interior region 1006 of the high-flow luer lock connector 1002 of FIGS. 10-14 causing the lugs or plurality of threads 1026 on an exterior of the female luer lock connector 1024 to engage the plurality of threads 1022 of the high-flow luer lock connector 1002. The engagement of the plurality of threads 1022, 1026 draws the female luer lock connector 1024 into the interior region 1006 of the high-flow luer lock connector 1002 until the exterior of the female luer lock connector 1024 engages and seals to the o-ring or washer 1020.

Typically, the female luer lock connector 1024 comprises an open end 1028 through which a substance such as insufflation gas may flow into or out of the female luer lock connector 1024. When the female luer lock connector 1024 engages the o-ring 1020, the o-ring 1020 seals against the open end 1028 of the female luer lock connector 1024 by surrounding and/or abutting the open end 1028, thereby creating a substantially airtight seal between the open end 1028 of the female luer connector 1024 and the first end 1014 of the extended passageway 1012 and placing the open end 1028 of the female luer connector 1024 in communication with the extended passageway 1012.

Typically, the diameter of the open end 1028 of the female luer lock connector 1024 and the diameter of the first end 1014 of the extended passageway 1012 are substantially equal. Due to the consistency in cross-section between the open end 1028 of the female luer lock connector 1024 and the first end 1014 of the extended passageway 1012, the substantially airtight seal and communication between the open end 1028 of the female luer connection 1024 and the extended passageway 412 of the high-flow luer connector 1002 may be accomplished without reducing the cross-sectional area through which the substance flows through the luer lock connection 1023, thereby preventing a substantial reduction in flow speed and a build up of pressure.

FIGS. 16-20 show a third embodiment of a high-flow luer lock connector 1602. The high-flow luer lock connector 1602 comprises a connector body 1604 that defines an interior region 1606 bounded by a cylindrical side wall 1608 and a base wall 1610. At the base wall 1610, the connector body 1604 further defines a lumen rim 1612 that extends into the interior region 1606. Typically, the lumen rim extends no more than 0.125 of an inch into the interior region 1606. It should be noted that in contrast to the second embodiment of the high-flow luer lock connector 1002 of FIGS. 10-14, the third embodiment of the high-flow luer lock connector 1602 typically does not comprise an o-ring or washer positioned at the base wall 1610.

The connector body 1604 additionally defines a rigid or semi-rigid extended passageway 1614 comprising a first end 1616 and a second end 1620. The extended passageway 1614 passes through the lumen rim 1612 and the connector body 1604 such that the first end 1616 of the extended passageway 1614 is positioned at the end of the lumen rim 1612. Additionally, the second end 1620 may comprise a taper, chamfer, or any other type of shape to reduce resistance created by a substance flowing into or out of the second end 1620

Typically, the extended passageway 1612 is operative to allow a substance to flow in either of two directions. In a first direction, a substance flows into the extended passageway 1614 at the first end 1616, flows through the lumen rim 1612 and connector body 1604 via the extended passageway 1614, and flows out of the extended passageway 1614 at the second end 1620. In a second direction, a substance flows into the extended passageway 1614 at the second end 1620, flows through the connector body 1604 and lumen rim 1612 via the extended passageway 1614, and flows out of the extended passageway 1614 at the first end 1616. These directions will generally correspond to introducing insufflation gas into an abdominal cavity of a patient or venting insufflation gas from the abdominal cavity of the patient.

The connector body 1604 additionally defines a plurality of threads 1622 on the cylindrical side wall 1608 operative to receive lugs or a plurality of threads defined on a corresponding female luer connector and place the corresponding female luer connector in position within the high-flow connector 1602.

Figure 21:
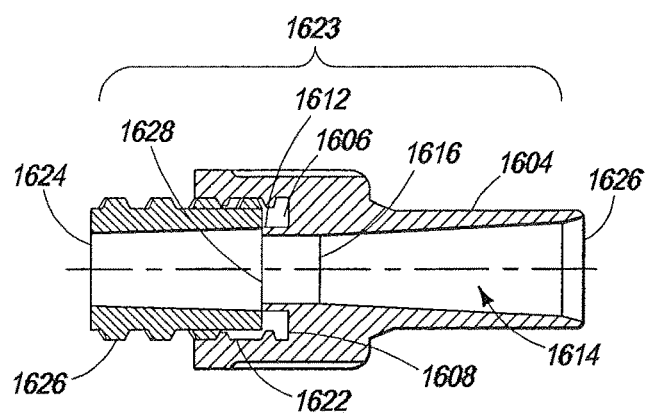
FIG. 21 is a side view of a cross-section of a luer lock connection utilizing the luer lock connector of FIG. 16.
Figure 22:
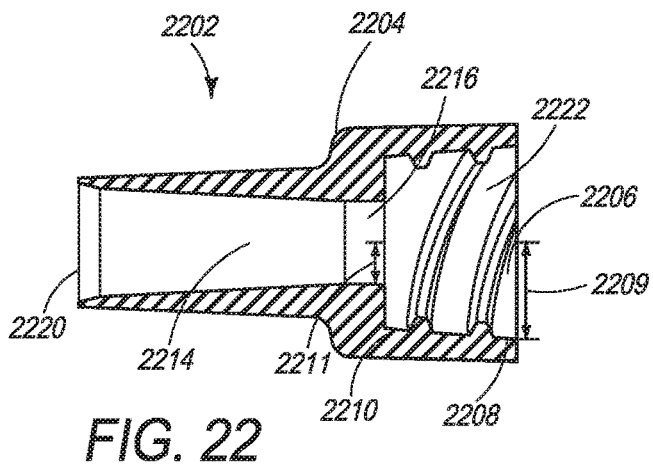
FIG. 22 is a side view of a cross-section of a fourth embodiment of a high-flow luer lock connector.
Figure 23:
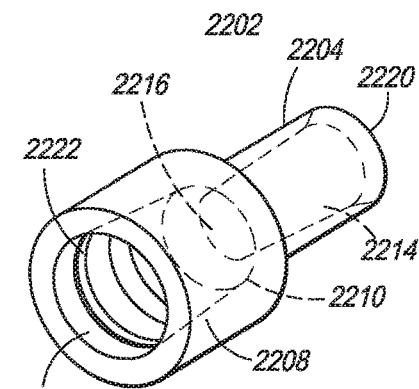
FIG. 23 is a perspective view of the high-flow luer lock connector of FIG. 22.
Figure 24:
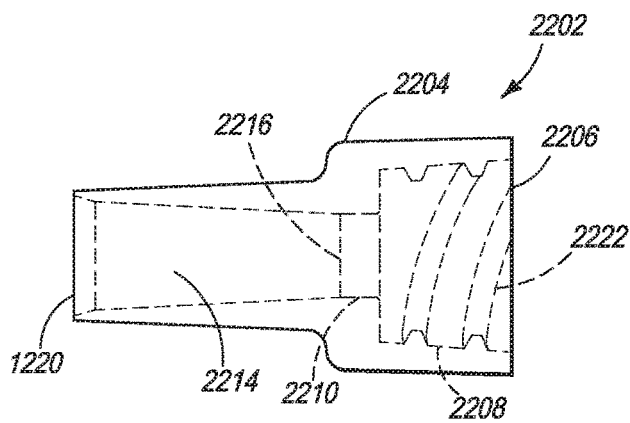
FIG. 24 is a side view of the high-flow luer lock connector of FIG. 22.
Figure 25:
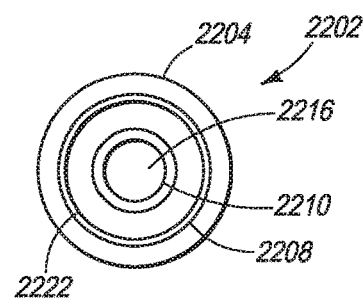
FIG. 25 is a front view of the high-flow luer lock connector of FIG. 22.
Figure 26:
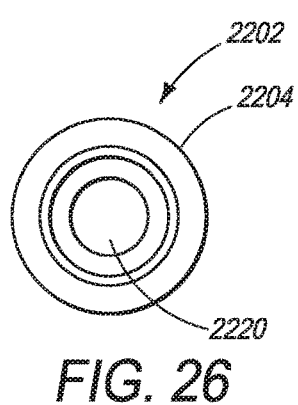
FIG. 26 is a rear view of the high-flow luer lock connector of FIG. 22.

As shown in FIG. 21, to establish a luer lock connection 1623 a female luer lock connector 1624 dimensioned according to ISO standards 594-1 or 594-2 is inserted into the interior region 1606 of the high-flow luer lock connector 1602 of FIGS. 16-20 causing the lugs or plurality of threads 1626 on an exterior of the female luer lock connector 1624 to engage the plurality of threads 1622 of the high-flow luer lock connector 1602. The engagement of the plurality of threads 1622, 1626 draws the female luer lock connector 1624 into the interior region 1606 of the high-flow luer lock connector 1602 until the exterior of the female luer lock connector 1624 engages the lumen rim 1612.

Typically, the female luer lock connector 1624 comprises an open end 1628 through which a substance may flow into or out of the female luer lock connector 1624. When the female luer lock connector 1624 engages the lumen rim 1612 defined by the connector body 1604, the lumen rim 1612 seals against the female luer connector 1624 by surrounding and/or abutting the open end 1628, thereby creating a substantially airtight seal between the open end 1628 of the female luer lock connector 1624 and the first end 1616 of the extended passageway 1014 and placing the open end 1028 of the female luer lock connector 1624 in communication with the extended passageway 1614.

Typically, the diameter of the open end 1628 of the female luer lock connector 1624 and the diameter of the first end 1616 of the rigid channel 1614 are substantially equal. Due to the consistency in cross-section between the open end 1628 of the female luer lock connector 1624 and the first end 1616 of the extended passageway 1614, the substantially airtight seal and communication between the open end 1628 of the female luer connection 1624 and the extended passageway 1614 of the high-flow luer connector 1602 may be accomplished without reducing the cross-sectional area through which the substance flows through the luer lock connection 1623, thereby preventing a reduction in flow speed and a build up pressure.

FIGS. 22-26 show a fourth embodiment of a high-flow luer lock connector 2202. The high-flow luer lock connector 2202 comprises a connector body 2204 comprising elastomeric material that defines an interior region 2206 bounded by a conic side wall 2208 and a base wall 2210. The conic side wall 2208 is created by tapering the side wall such that a radius 2209 of an opening of the interior region 2206 is greater than a radius 2211 of the base wall 2210.

The connector body 2204 further defines a rigid or semi-rigid extended passageway 2214 comprising a first end 2216 and a second end 2220. The first end 2216 is flush with the base wall 2210 such that the extended passageway 2214 does not extend into the interior region 2206. Additionally, the second end 2220 may comprise a taper, chamfer, or any other type of shape to reduce resistance created by a substance flowing into or out of the second end 2220.

Typically, the extended passageway 2214 is operative to allow a substance to flow in either of two directions. In a first direction, a substance flows into the first end 2216 of the extended passageway 2214, through the connector body 2204 via the extended passageway 2214, and out of the second end 2220 of the extended passageway 2214. In a second direction, a substance flows into the second end 2220 of the extended passageway 2214, through the connector body 2204 via the extended passageway 2214, and out of the first end 2216 of the extended passageway 2214. These directions will generally correspond to introducing insufflation gas into an abdominal cavity of a patient or venting insufflation gas from the abdominal cavity of the patient.

In one embodiment, the connector body 2204 additionally defines a plurality of threads 2222 on the conic side wall 2208 operative to receive lugs or a plurality of threads defined on a corresponding female luer connector and place the corresponding female luer connector in position within the high-flow connector 2202. However in other embodiments, the high-flow connector 2202 may utilize internal ribs defined on the conic side wall 2208 to conform around the female luer to secure the high-flow luer connector 2202 and corresponding female luer connector.

Figure 27:
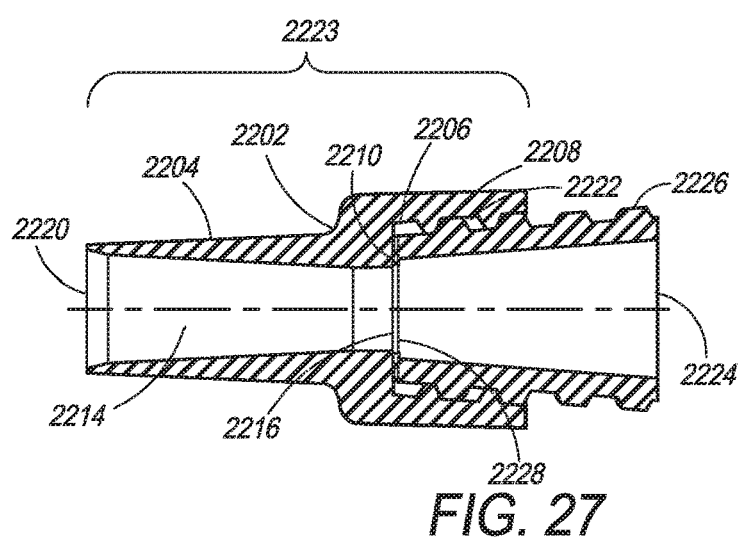
FIG. 27 is a side view of a cross-section of a luer lock connection utilizing the luer lock connector.

As shown in FIG. 27, to establish a luer lock connection 2223 a female luer lock connector 2224 dimensioned according to ISO standards 594-1 or 594-2, is inserted into the interior region 2206 of the high-flow luer lock connector 2202 of FIGS. 22-26 causing lugs or a plurality of threads 2226 on an exterior of the female luer lock connector 2224 to engage the plurality of threads or internal ribs 2222 of the high-flow luer lock connector 2202. The engagement of the plurality of threads or internal ribs 2222, 2226 draws the female luer lock connector 2224 into the interior region 2206 of the high-flow connector 2224 until the exterior of the female luer lock connector 2224 engages the layer of elastomeric material 2212 of the base wall 2210.

Typically, the female luer lock connector 2224 comprises an open end 2228 through which a substance may flow into or out of the female luer lock connector 2224. When the female luer lock connector 2224 engages the layer of elastomeric material 2212 of the base wall 2210, the layer of elastomeric material 2212 seals against the female luer connector 2224 by surrounding and/or abutting the open end 2228, thereby creating a substantially airtight seal between the open end 2228 of the female luer connector 2224 and first end 2216 of the extended passageway 2214 and placing the open end 2228 of the female luer lock connector 2224 in communication with the extended passageway 2214.

Typically, the diameter of the open end 2228 of the female luer lock connector 2224 and the diameter of the first end 2216 of the extended passageway 2214 are substantially equal. Due to the consistency in cross-section between the open end 2228 of the female luer lock connector 2224 and the first end 2216 of the extended passageway 2214, the substantially airtight seal and communication between the open end 2228 of the female luer connection 2224 and the extended passageway 2214 of the high-flow luer connector 2202 may be accomplished without reducing the cross-sectional area through which the substance flows through the luer lock connection 2223, thereby preventing a reduction in flow speed and a build up pressure.

It is therefore intended that the foregoing detailed description be regarded as illustrative rather than limiting, and that it be understood that it is the following claims, including all equivalents, that are intended to define the spirit and scope of this invention.

The invention claimed is:

1. A luer lock connector system for use in an insufflation system, comprising:
   a female luer lock connector comprising a passageway that is configured to sustain a flow rate of insufflation gas of at least 26 liters per minute;
   a male luer lock connector comprising:
      a male luer lock connector body comprising elastomeric material;
      a conic interior region defined by the connector body, the interior region bounded by a conic side wall and a base wall; and
      an extended passageway defined by the connector body comprising a first end and a second end, the extended passageway passing through the connector body at the base wall, the extended passageway in communication with the interior region to allow insufflation gas to flow through the interior region and extended passageway;
      wherein the base wall is flat from the conic side wall to the first end of the extended passageway passing through the base wall; and
   wherein an open end of the conic interior region of the male luer lock connector is configured to receive and to establish a luer lock connection with the female luer lock connector; and
   wherein the open end of the conic region of the male luer lock connector is configured to position an exterior of an end of the female luer connector adjacent to the base wall such that the first end of the extended passageway of the male luer lock connector is in communication with the end of the female luer lock connector positioned adjacent to the base wall such that insufflation gas flows between the extended passageway of the male luer lock connector and the passageway of the female luer lock connector at a sustained flow rate of at least 26 liters per minute.

2. The luer lock connector system of claim 1, wherein the male luer lock connector further comprises:
   a plurality of internal ribs defined on the conic side wall of the conic interior region.

3. The luer lock connector system of claim 2, wherein:
   the female luer lock connector defines a plurality of threads or lugs on an exterior of the female luer lock connector;
   the male luer lock connector defines a plurality of internal ribs that is configured to receive the plurality of threads or lugs defined on the female luer lock connector and position the exterior of the female luer lock connector securely against the elastomeric material of the base wall; and
   the elastomeric material of the base wall is operative to seal against at least an opening of the female luer lock connector and place the opening of the female luer lock connector in communication with the first end of the extended passageway such that insufflation gas may flow through the female luer lock connector and the male luer lock connector.

4. The luer lock connector system of claim 3, wherein the elastomeric material of the base wall of the male luer lock connector is operative to abut at least the opening of the female luer lock connector.

5. The luer lock connector system of claim 1, wherein the elastomeric material comprises PVC.

6. The luer lock connector system of claim 1, wherein the elastomeric material comprises silicone.

7. The luer lock connector system of claim 1, wherein when the male luer lock connector receives the female luer lock connector, the male luer lock connector is configured to form a secure, leak-free connection with the female luer lock connector for the transfer of insufflation gas to a veress needle.

8. The luer lock connector system of claim 1, wherein when the male luer lock connector receives the female luer lock connector, the male luer lock connector is configured to form a secure, leak-free connection with the female luer lock connector for the transfer of insufflation gas to a trocar.

9. The luer lock connector system of claim 1, wherein when the male luer lock connector receives the female luer lock connector, the male luer lock connector is configured to form a secure, leak-free connection with the female luer lock connector for the transfer of insufflation gas from a gas delivery system.

10. The luer lock connector system of claim 1, wherein when the male luer lock connector receives the female luer lock connector, the male luer lock connector is configured to form a secure, leak-free connection with the female luer lock connector for the transfer of fluids or gasses from an insufflation system.

\* \* \* \* \*

UNITED STATES PATENT AND TRADEMARK OFFICE
CERTIFICATE OF CORRECTION

PATENT NO. : 10,086,154 B2
APPLICATION NO. : 14/076842
DATED : October 2, 2018
INVENTOR(S) : Robert R. Mantell Page 1 of 1

It is certified that error appears in the above-identified patent and that said Letters Patent is hereby corrected as shown below:

On the Title Page

Please correct the Related U.S. Application Data to reflect the following:
(63) Continuation of application No. 12/776,647, filed on May 10, 2010, now Pat. No. 8,613,738, which is a continuation of application No. 11/418,838, filed on May 5, 2006, now Pat. No. 7,740,288.
(60) Provisional application No. 60/679,452, filed on May 9, 2005.

Signed and Sealed this
Twenty-ninth Day of December, 2020

Andrei Iancu
*Director of the United States Patent and Trademark Office*